United States Patent [19]
Himmler et al.

[11] Patent Number: 6,033,881
[45] Date of Patent: Mar. 7, 2000

[54] METHOD FOR ONE STEP ISOTHERMAL NON-TRANSCRIPTION BASED AMPLIFICATION OF NUCLEIC ACIDS

[76] Inventors: Gottfried Himmler, Colloredogasse 29/13, A-1180 Vienna; Thomas Schlederer, Dragonerweg 21, A-1220 Vienna, both of Austria

[21] Appl. No.: 08/973,965

[22] PCT Filed: Jun. 13, 1996

[86] PCT No.: PCT/AT96/00106

§ 371 Date: Apr. 6, 1998

§ 102(e) Date: Apr. 6, 1998

[87] PCT Pub. No.: WO97/00330

PCT Pub. Date: Jan. 3, 1997

[30] Foreign Application Priority Data

Jun. 13, 1995 [AT] Austria ..................................... 1007/95

[51] Int. Cl.[7] .............................. C12P 19/34; C12Q 1/68; C07H 21/04
[52] U.S. Cl. ............................ 435/91.2; 435/6; 435/91.1; 435/91.21; 536/23.1; 536/24.3; 536/24.31
[58] Field of Search ............................. 435/6, 91.1, 91.2, 435/91.21, 91.5, 91.51, 91.52; 536/23.1, 24.3, 24.31, 24.32

[56] References Cited

U.S. PATENT DOCUMENTS

| | | | |
|---|---|---|---|
| 4,683,202 | 7/1987 | Mullis | 435/91.1 |
| 5,273,881 | 12/1993 | Sena et al. | 435/6 |
| 5,322,770 | 6/1994 | Gelfand et al. | 435/6 |
| 5,527,670 | 6/1996 | Stanley | 435/6 |

FOREIGN PATENT DOCUMENTS

| | | |
|---|---|---|
| 497272 | 1/1992 | European Pat. Off. . |
| 90/01069 | 2/1990 | WIPO . |
| WO 90/10064 | 9/1990 | WIPO . |
| WO93/13220 | 7/1993 | WIPO . |
| 94/03635 | 2/1994 | WIPO . |
| 95/25180 | 9/1995 | WIPO . |

OTHER PUBLICATIONS

Kievits et al J. of Virol. Methods vol. 35 pp. 273–286, 1991.
Walker et al PNAS vol. 89 pp. 392–396, 1992.
*The Journal of Biological Chemistry*, M. Iyer et al., "Accelerated Hybridization of Oligonucleotides to Duplex DNA", vol. 270, No. 24, Issue of Jun. 16, pp. 14712–14717, 1995.
*The Journal of Biological Chemistry*, E. Kmiec, et al., "DNA Strand Exchange in the Absence of Homologous Pairing", vol. 269, No. 13, Issue of Apr. 1, pp. 10163–10168, 1994.
*Critical Review in Biochemistry and Molecular Biology*, J. Wetmur, "DNA Probes: Applications of the Principles of Nucleic Acid Hybridization", 26(3/4):227–259 (1991).
*Bioconjugate Chem.*, D. Corey, et al., "Strand Invasion by Oligonucleotide–Nuclease Conjugates", 1995, 6, 93–100.

*Primary Examiner*—Kenneth R. Horlick
*Assistant Examiner*—Jeffrey Siew
*Attorney, Agent, or Firm*—Burns, Doane, Swecker & Mathis, L.L.P.

[57] ABSTRACT

The present invention relates to a process for the transcriptionless amplification of nucleic acids or nucleic acid sequences by means of enzymes in which the nucleic acids or sequences are divided at least partially into their individual strands before amplification and/or transcribed and the reaction mixture contains oligonucleotides with a base sequence essentially complementary to those of the ends of the nucleic acids or sequences to be amplified, where said oligonucleotides can, in certain conditions, form starting points and/or chemical components for the synthesis of nucleic acids and are built into the amplification product to be formed. The product of the components itself again corresponds to the nucleic acid or sequence to be amplified. The reaction product formed from the oligonucleotide components, possibly from the templates and other chemical components, reacts again in one step with the oligonucleotide components, the reaction being conducted substantially isothermally.

17 Claims, 1 Drawing Sheet

Figure 1

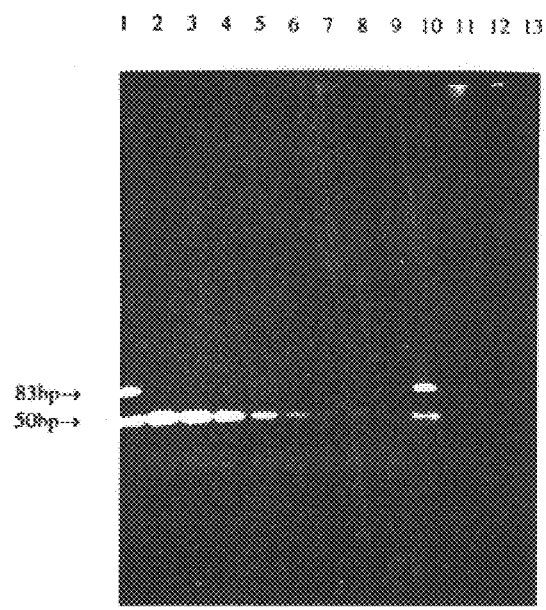

Figure: Agarose electropherogram of DNA-fragments, stemming from reverse transcription of RNA with HIV I-sequenz and subsequent isothermal amplification.

Lane 1 and 10: Reference fragments with 50 and 83 basis lengths;
Lane 2, 3, 4, 5, 6, 7, 8: Detection of 1 fmol, 100 amol, 10 amol, 1 amol, 0.1 amol, 0.01 amol and 0.001 amol RNA with HIV I-sequenz.
Lane 9 and 11: Blind control of water without RNA.
Lane 12: Blind control of isothermal amplification without reverse transcriptase.
Lane 13: Blind control without reverse transcriptase and without Taq DNA-polymerase.

METHOD FOR ONE STEP ISOTHERMAL NON-TRANSCRIPTION BASED AMPLIFICATION OF NUCLEIC ACIDS

BACKGROUND OF THE INVENTION (i) Field of Invention

The present invention relates to the field of molecular biology and recombinant DNA-technology (genetic engineering). The invention allows a simplified in vitro synthesis of nucleic acids. The herein described methods are especially applicable to the amplification of nucleic acids with primer-dependent DNA/RNA-polymerases, DNA- and RNA-ligases. The invention has numerous applications in molecular biology, medical diagnostics, environmental and forensic analysis.

The invention relates especially to a process for isothermal, non-transcription based, amplification of nucleic acids and nucleic acid sequences respectively, by means of enzymes whereby the nucleic acids and nucleic acid sequences respectively, may be at least partially separated into single strands and/or transcribed.

The amplification proceeds by enzymatic incorporation of at least two oligonucleotide building blocks with a sequence essentially complementary to the sequence of the ends of the complementary strands of the nucleic acid or nucleic acid sequence to be amplified, wherein the product of the building blocks itself corresponds to the nucleic acid and nucleic acid sequence to be amplified.

(ii) Description of Related Art

The in vitro-amplification of nucleic acids, such as DNA and RNA and nucleic acid sequences, respectively, has many applications and may be performed in different ways (amplification in this document means a substantial amplification, i.e. more than doubling of the starting material).

The principle of amplification of DNA by means of polymerase activity has been described in detail by Kleppe et al., J. Mol. Biol. 56: 341 (1971). Accordingly, oligonucleotides are used as starting points for enzymatic DNA-synthesis such that the product of this synthesis may be used as template for further synthesis. According to this principle the complementary nucleic acids strands have to be separated repeatedly between the single steps of the synthesis. U.S. Pat. No. 4,683,202 describes the realization of this principle.

Regarding the applied temperature one may distinguish especially two processes: processes with cycling temperature changes between amplification temperature and denaturing (strand separation) temperature, wherein the nucleic acids or the nucleic acid sequences prior to the amplification step have to be separated essentially completely into single strands. The other amplification processes work isothermally.

The polymerase chain reaction (PCR), for example, belongs to the first group of temperature cycling processes, wherein a nucleic acid sequence can be amplified exponentially in such a reaction where the temperature is subjected to a cyclic change. For such an amplification, usually a thermostable polymerase is used [e.g. Saiki et al., Science, 230, 1350–1354 (1985), Saiki et al., Science, 239, 487 (1988), respectively].

According to U.S. Pat. No. 4,683,195 (Mullis et al.) one can perform in a temperature cycling process the strand separation following the amplification step by any suitable denaturation method, it may be chemically, physically or enzymatically. In the referred document physical strand separation methods are preferred, e.g. heating the nucleic acid until complete denaturation (>99%), i.e. separated into two single strands. A typical heat denaturation is performed at temperatures between 90° C. and 105° C. and lasts generally between 0.5 and 3 minutes. Preferred temperatures are between 90° C. and 100° C. for 0.5 to 3 minutes. When using a thermolabile enzyme (U.S. Pat. No. 4,683,202) one has to add fresh enzyme after each strand separation by heat. By using a thermostable enzyme one does not need to interrupt the thermocycling for enzyme addition. The process is performed by means of temperature cycling apparatus "simultaneously".

A further process in the group of thermocycling processes is the so called ligase chain reaction (LCR) e.g. according to F. Barany in Proc. Natl. Acad. Sci. USA, 88, 189–193 (1991), wherein the process, as in PCR, leads to a non-linear amplification of the starting nucleic acid, also a cyclic temperature change proceeds between an amplification temperature and a denaturation temperature and a thermostable ligase is used as enzyme (WO 90/01069 and EP-A 320308). A special form of LCR is the "gap-filling LCR", in which process, in addition to the ligase also a polymerase is used. In such a reaction only the products of the polymerase reaction are used a substrates for the ligase (U.S. Pat. No. 5,427,930).

One may also use several similar enzymes with slightly different properties in one reation to achieve special results, which cannot be achieved with only one enzyme. The amplification of long DNA-stretches is an example for such a reaction (Barnes, W. M., Proc. Natl. Acad. Sci. USA, 91, 2216–2220, (1994)).

On the other hand, isothermal processes, such as e.g. the self sustained sequence reaction (3SR) are well known in the state of the art, e.g. from E. Fahy et al., PCR Meth. Appl. 1, 25–33, (1991); D. Kwoh et al., Proc. Natl. Acad. Sci. (USA) 86, 1173–7 (1989); WO 88/10315 (T. R. Gingeras et al.); EP-A 0 329 822 (H. I. Miller et al.); and J. van Brunt, Bio/Technology 8, 291–4(1990); U.S. Pat. Nos. 5,409,818, 5,399,491 and 5,194,370).

These processes have in common that they can be performed isothermally, however, one needs several different enzymes for the amplification (e.g. reverse transcriptase, RNaseH, RNA-polymerase) as the amplification step is performed via transcription (RNA to DNA, and DNA to RNA, respectively). A further disadvantage is also the lower specificity of such isothermal processes of the state of the art as there are no thermostable enzymes used. If RNA-products are the result, a further disadvantage is that handling is more difficult (size fractionation is not as simple as with DNA). There is also no contamination control system available.

The following references describe further alternative processes for the amplification of nucleic acids and nucleic acid sequences, respectively, by means of specific enzyme systems (restriction endonucleases, Q-beta-replicases): G. T. Walker et al., Proc. Natl. Acad. Sci. (US) 89, 392–6 (1992); U.S. Pat. No. 5,356,774 (V. D. Axelrod et al.); and P. Knight, Bio/Technology 7, 609–10 (1989).

WO 90/10064 and WO 91/03573 describe the use of the origin of replication of phage phi29 for the isothermal amplification of nucleic acids.

The so-called strand displacement amplification (U.S. Pat. Nos. 5,455,166 and 5,422,252) is based on the strand displacement activity of polymerases, which start to displace one of the complementary nucleic acid strands at a certain region (which is defined by primers and specific endonucleases in the reaction mixture) while at the same time synthesizing a new complementary strand.

A simple, isothermal strand displacement amplification process is described in EP-A 0 676 476. In this process only a single enzyme is needed, which is a polymerase. However, one needs at least 2 oligonucleotides per strand, i.e. altogether at least four oligonucleotides, for amplification.

A special form of PCR is nested-PCR (e.g. U.S. Pat. No. 5,340,728, EP-A 0 519 338, U.S. Pat. No. 4,683,195, U.S. Pat. No. 5,314,809).

Another special form of PCR is RT-PCR, wherein a RNA template is first transcribed into cDNA. One can use an enzyme which exhibits reverse transcriptase activity as well as DNA polymerase activity (e.g. U.S. Pat. No. 5,322,770).

Although all these methods have found their place in research (PCR must not be missed in a modern molecular biology laboratory) they are complex and are highly demanding so that they are hardly to be described as routine method. Also, there are high equipment—and reagent costs linked to these methods, since especially for thermocycling expensive high performance-thermostats are necessary (cf. R. Hoelzel, "Trends in Genetics", 6, 237–238 (1990); or U. Linz, Biotechniques, 9, 286–292 (1990), and on the other hand for the isothermal methods expensive enzymes have to be used.

DEFINITIONS

Isothermal: "Substantially isothermal" and "at essentially the same temperature" means a deviation from the given temperature in the range of the deviation of a commercial thermostate.

Starting material: In the process according to the present invention every nucleic acid or nucleic acid sequence in purified or non-purified form may be used as starting material, provided it contains (or it is assumed that it contains) essentially a nucleic acid sequence which is specific for the oligonucleotides building blocks employed. For the process according to the present invention DNA or RNA (including mRNA, rRNA, tRNA, etc.) in single stranded or double stranded form may be used. Moreover, also a DNA-RNA hybrid may be used as template. A mixture of these nucleic acid species may be used as well as nucleic acid coming from previous amplifications. It may then be amplified by means of the same or different oligonucleotides as in the previous amplification.

The specific nucleic acid or nucleic acid sequence to be amplified may be part of a larger molecule or may be such that the molecule corresponds to the specific sequence of the whole nucleic acid.

It is not necessary for the sequence to be amplified to be in pure form, it may also be a fracture of a complex mixture (e.g. as part of a genome). This genome itself may also only be part of a biological sample (e.g. cells or tissue).

The starting nucleic acid or nucleic acid sequence, respectively, may contain one or more specific nucleic acid sequences (which may be identical or different). Thus the method of amplification is not only suitable to produce large amounts of a speficic nucleic acid, but may also be used to simultaneously amplify several subsequences of the starting nucleic acid or—sequence in one reaction vessel.

The nucleic acid, which may have been separated into single strands (denatured) before the amplification reaction, may come from different sources, e.g. from plasmids such as pBR322, from cloned DNA or RNA, from chemically synthesized DNA or RNA, from natural DNA or RNA of any origin (e.g. bacteria, yeasts, fungi, viruses and organelles; or from higher organisms such as plants animals or human beings). DNA or RNA may be extracted from e.g. blood, body fluids, plant saps, media or tissues by a number of techniques (cf. e.g. "Molecular Cloning. A Laboratory Manual", J. Sambrook et al., Cold Spring Harbor, Laboratory Press, New York (1989)—one may also use non-extracted parts of tissues or cells. In principle, one may amplify—by means of the process according to the present invention—any specific nucleic acid.

Chemical building blocks: In the present document the term "chemical building blocks" means such which are or may be used for the enzymatic synthesis of nucleic acids, e.g. deoxyribonucleotide triphosphates, ribonucleotide triphosphates, oligonucleotides (such as ribooligonucleotides or deoxyribonucleotides). One may also use modified building blocks, e.g. blocks which carry a certain marker such as biotin and the like or reactive groups such as phosphate groups. It is contemplated that one may also use smaller building blocks such as e.g. parts of nucleotides and nucleosides and derivatives thereof.

Oligonucleotide building blocks: The term "oligonucleotide" is used herein for naturally occuring or synthetic molecules, which contain at least two deoxyribonucleotides or ribonucleotides or derivatives thereof. The modification may be within the base and within the backbone of the oligonucleotide (e.g. peptide nucleic acids, hexose phosphates, etc.).

The actual size of the oligonucleotides is dependent on several factors, which in turn are dependent on the respective use or function of the oligonucleotides. Oligonucleotides may be chemically synthesized or produced by preparing or cloning of DNA- or RNA-sequences.

Oligonucleotide building blocks are oligonucleotides which are used in the present invention as chemical building blocks. An oligonucleotide building block therefore is a nucleic acid, a nucleic acid sequence or an oligonucleotide, which, under suitable conditions (i.e. influence of enzymes, presence of necessary chemical building blocks such as e.g. further oligonucleotide building blocks nucleotide triphosphates, buffer conditions, e.g. pH, ionic strength, cofactors, etc.) and at the appropriate temperature may serve as chemical building block for the synthesis of a nucleic acid.

Concerning the number of complementary base sequences between oligonucleotide building blocks and template it is only necessary that a sufficient number of bases at both ends of the specific nucleic acid sequence to be amplified is essentially known, so that at least two oligonucleotide building blocks, may be synthesized of which at least one may hybridize to the respective complementary strand. The relative position on the sequence is preferentially selected such that the product which is built up by one oligonucleotide building block (in polymerase-catalyzed amplification) or by two oligonucleotide building blocks (in ligase-mediated catalyzed reactions) respectively, may serve as template for the enzymatic extension (in polymerase catalyzed reactions) of the respective other oligonucleotide building block or for the joining (in ligase catalyzed reactions) for the respective other oligonucleotide building blocks.

Oligonucleotide building blocks may stem from natural sources, e.g. restriction digested DNA or they may be chemically synthesized and/or be produces enzymatically. The exact length of the oligonucleotide building blocks is dependent on several factors, such as e.g. temperature, template sequence, etc. oligonucleotide building blocks have, in general, a length of 15 to 40 bases, however, they may also be shorter or longer. In general shorter oligonucleotide building blocks need lower temperature for an efficient reaction. In any case, the oligonucleotide building blocks used in the process according to the present invention have to be substantially complementary to the respective specific sequences to be amplified.

An oligonucleotide building block does not need to be exactly complementary to its respective template strand. It is e.g. possible to add non-complementary nucleotide sequences and/or markers (such as haptens or enzymes) at the outer ends of the oligonucleotide building blocks which should react.

Transcription: Transcription is the process of building a RNA strand by using a DNA strand as template. A special case of transcription is the reverse transcription, in which a DNA strand is produced (built) using a RNA strand as a template. "Transcription" in the present description means a process which leads from one nucleic acid species (RNA or DNA) to the respective other nucleic acid species (DNA or RNA).

Template: Every nucleic acid or nucleic acid sequence, which may serve as basis for the synthesis of the respective complementary strand is referred to as "template". The starting nucleic acid as well as the intermediate and reaction products may be template.

Mutation: A mutation is a change in the base content of a nucleic acid. The bases present may be natural bases, the difference may be the deletion, the exchange or the addition of bases. Moreover, the base composition of a nucleic acid may be substantially the same and the change may be related to a chemical modification of the molecule. It may also be a combination of the types mentioned above.

Enzyme: Enzymes are usually polypeptides, which catalyze a chemical reaction. However, it is possible to find enzymatic activity in other classes of compounds which may be used as enzymes (e.g. RNA, synthetic polymers). "Enzyme" is also understood to comprise a mixture of different enzymes with similar properties.

Helper oligonucleotides: Helper oligonucleotides are oligonucleotides, which improve a chemical reaction without being used as a chemical building block in such a reaction.

Reaction product: The reaction product is a double stranded molecule of nucleic acid which has been produced from the chemical building blocks added by enzymatic activity. The reaction product may also partly consist of the template.

SUMMARY OF THE INVENTION

The present invention relates to a process for transcription-free amplification of nucleic acids or nucleic acid sequences respectively, by means of enzymes, wherein the nucleic acids or nucleic acid sequences respectively, if necessary, are at least partially separated into single strand and/or transcribed before amplification and the reaction mix contains oligonucleotides with a base sequence substantially complementary to the base sequences of the ends of the nucleic acid or nucleic acid sequence to be amplified, which oligonucleotides, under appropriate conditions, may form starting points and/or chemical building blocks for the nucleic acid synthesis and are built into the amplification product to be formed, wherein the product from these building blocks itself corresponds to the nucleic acid or nucleic acid sequence to be amplified, characterized in that the reaction product, which was built up by the oligonucleotide building blocks, optionally by template and optionally by further chemical building blocks, reacts in one step again with the oligonucleotide building blocks, the reaction being performed sustantially isothermal.

BRIEF DESCRIPTION OF THE DRAWING

FIG. 1 is an agarose electropherogram of DNA—fragments, stemming from reverse transcription of RNA with HIV I—sequence and subsequent isothermal amplification.

DETAILED DESCRIPTION PREFERRED EMBODIMENTS

It is the purpose of the present invention to overcome the known disadvantages of the conventional processes such as PCR, LCR or 3SR and to provide a simple, cost efficient process of the kind described above.

This task is solved according to the present invention by performing the process substantially isothermal and by using only one enzyme.

In such a isothermal process the amplification proceeds while nucleic acids or nucleic acid fragments remain double stranded, i.e. the hydrogen bonding between the base pairs of the complementary, nucleic acids to be amplified remain mostly intact. In other words this means that during amplification complementary nucleic acids and nucleic acid fragments, respectively, are present as double strands.

All reactants, nucleotide triphosphates, oligonucleotide building blocks, product, template and the enzyme are in a steady state equilibrium regarding one another and all other reaction components. The reaction conditions and especially the reaction temperature are selected according to the present invention so that also the amplification product is preferrably double stranded. Although the reaction mechanism is not yet clear one may assume, according to the data and results of experiments available, it is contemplated that in the process according to the present invention the oligonucleotide building blocks are adding already to the double stranded form of the starting nucleic acid and nucleic acid fragments, respectively, which is in contradiction to the conventional opinion about such molecular mechanisms. Therefore, the mandatory separation of nucleic acid or nucleic acid fragments or, if the reaction proceeds of the intermediate products of the reaction into single strands, which is essential for the conventional processes such as PCR, LCR, 3SR etc., is not necessary.

Usual processes are based on a separation of the reaction intermediate products into their single strands, and then hybridisation of the oligonucleotides with these single strands. The process according to this invention however, is based upon the surprising observation that the oligonucleotides react at a given temperature with the starting material and with the amplification product, respectively, in one step, and that as a result of the enzymatic catalysis again amplification products result from these reaction products. The essential and important difference to the processes of the state of the art is that in PCR or LCR and related processes single strands are prepared by heat denaturation to present the oligonucleotides a single strandes template, onto which the primers and oligonucleotide building blocks then hybridize.

In the process of the invention however, the fact is exploited that when a dynamic equilibrium is present, the reaction products can be favorized if a reaction component is added in surplus. This kind of reaction is called strand invasion (or strand exchange) and has been described on D-form DNA after the filing date of the priority application to the present invention (Iyer, M. et al. J. Biol. Chem. 270,14712, 1995). However, the strand invasion could not be observed on B-form of DNA the most common form of DNA. In the present invention the B-form of nucleic acid helix is destabilized by heat, so that it is surprisingly prone to strand exchange reaction. There are also peptides described, which improve the strand exchange reaction (Corey, D. R., J. Am. Chem. Soc., 9373 (1995)). Such peptide sequences may also be used in the present invention. It is contemplated that peptide nucleic acids may be used to improve the strand exchange reaction (Iyer, M. et al., J. Biol. Chem. 270, 14712 (1995)).

Thus in the process according to the present invention not single stranded molecules are presented as templates, the oligonucleotide building blocks react in such an isothermal reaction by itselfs with the double stranded amplification product to give new, incomplete reactands which in turn react instantly with the respective enzymes and all the other reaction partners autocatalytically to give new amplification products.

For the process according to the present invention different enzymes may be used either alone or in combination. If polymerases are used, the synthesis starts at the 3'-end of the oligonucleotide building block and proceeds in direction to the 5'-end along the template. It is contemplated that enzymes could exist which start the synthesis at the 5'-end of the primer and proceed in direction to the 3'-end. Such enzymes could also be used in the process according to the present invention. One could also contemplate that a oligonucleotid building block dependent RNA-polymerase is used as enzyme. If ligase is used, one uses generally in part oligonucleotide building blocks which have phosphate groups on their ends. It is also contemplated that one could use a mixture of similar enzymes or a mixture of different enzymes in a reaction to get specific amplifications (e.g. two or more different polymerases or polymerases and ligases). The specific nucleic acid or—sequence is produced by using a nucleic acid containing sample, which contains this specific sequence (or a part thereof) as a template. If the nucleic acid or—sequence to be produced a DNA, in case of using polymerase the four nucleotide triphosphates to be preferably employed are dATP, dCTP, dGTP and TTP.

The oligonucleotide concentration necessary for the reaction may vary but is usually higher than the template concentration (expressed in molar ratios). A large molar excess usually improves the reaction.

Optionally, a initial step of the process according to the present invention may be the denaturation (strand separation) or the transcription of the nucleic acid, so that an extensive contact between template strands, oligonucleotide building blocks, optionally nucleotide triphosphates and respective enzymes preferably polymerases and ligases during the subsequent cooling to the reaction temperature is possible. If not yet in the reaction solution, the chosen enzyme and the needed chemical building blocks are then added and the reaction mix is then brought to the appropriate reaction temperature. The reaction conditions, especially the reaction temperature is selected such that by taking advantage of the dynamic equilibrium between amplification product and chemical building blocks amplification is possible without strand separation. It is contemplated that the oligonucleotides used directly hybridize into the double strand form of the amplification product onto their complementary binding sites thus opening the double stranded form of the amplification product like a zipper.

The specific reaction temperature is usually chosen higher than the calculated melting temperature of the oligonucleotide building blocks, because of specifity.

The melting temperature of the oligonucleotide building blocks may be calculated in different ways, however, the optimal amplification temperature is dependent on many other factors (such as e.g. ionic strength of the buffer, concentration of the oligonucleotide building blocks, length and base composition of the template, etc.).

It is advantageous if the oligonucleotide building blocks are situated on the template as closed together as possible. Preferably so that the amplification product has the same size or is not substantially bigger than the sum of the length of the oligonucleotides used.

According to the present invention also reagent kits are provided, which contain oligonucleotide building blocks for use in the process of the present invention, whereas the difference of the melting temperatures between the oligonucleotide building blocks and the expected product is not higher than 25° C., preferably not higher than 20° C. and more preferably not higher than 15° C.

It is especially preferred if the difference of the melting temperature between the oligonucleotide building blocks and the expected product is not higher than 10° C., preferably not higher than 5° C.

For diagnostic methods it is best if the base sequence of the oligonucleotide building blocks is exactly complementary to at least a part of the target sequence.

The advantage of the process according to the present invention lies especially in the fact that there is no necessity of thermocycling, so that there is no need for expensive instrumentation, it is easier to standardize, one can do higher volume reactions (1 ml and more) and finally, that there is only one enzyme necessary. The process according to the present invention may of course also be used during conventional processes such as PCR and LCR as well as related processes. The temperature of the amplification step is then preferably above the calculated melting temperature of the oligonucleotides used.

It is contemplated that there may be many special forms of the present invention, e.g. nested, i.e. there is a first amplification with outher primers building blocks, afterwards parts of the amplification product are further amplified. A coupling of the amplification with a reverse transcription in one reaction tube is also possible.

The detection of the amplification product may be done in principle similar as in PCR. Especially suited seem fluorescence methods, which are based on energy transfer (Förster, T., Discuss. Faraday Soc., 27, 7 (1959)) or fluorescence polarization of one or two marked oligonucleotide building blocks. It is also contemplated that one may use fluorescence methods in which marked chemical building blocks have been incorporated during amplification and this incorporation is detected fluorimetrically or luminometrically.

The process according to the present invention will now be explained by way of several examples, however it is not bound only to these examples.

EXAMPLE 1
Amplification of a Linear, Single Stranded DNA

This example shows that it is possible to enzymatically propagate a certain single stranded DNA-molecule in vitro. By means of two oligonucleotide building blocks, which hybridize to two complementary DNA strands a double stranded product is formed. There is no common repeated change of the reaction temperature between amplification and denaturation temperature at all. All techniques and methods which are not described in detail are standard techniques which are described in collections of methods for genetic engineering or molecular biology (such as e.g. "Molecular Cloning. A laboratory manual"; Sambrook et al.; Cold Spring Harbor Laboratory Press, New York (1989; ISBN 0-87969-309-6).

1.1. Reaction Mix

50 µl reaction mixes were each transferred with a pipette into 0,5 µl reaction tubes (Eppendorf, Safe-Lock). The reaction mixes had the following composition:

10 mM $(NH_4)_2SO_4$
20 mM Tris-HCl (pH 8.8 at 25° C.)
2 mM $MgSO_4$
each 200 µM TTP, dGTP, dATP and dCTP (PROMEGA, Wisc.,USA) 0.1% (w/v) Triton X-100 (SERVA, Germany)
10 pmol oligonucleotide building block u676 [SEQ ID NO.: 1]:

5'-dgAgCCTTCAACCCAgTCAgCTCCTTCCggTgggCgCggggC-3'

10 pmol oligonucleotide building block 17554 [SEQ ID NO.: 2]:

5'-dCgCCgAAAATgACCCAgAgCgCTgCCg-gCACCTgTCCTACgAgTTgCATg-3'

1 fmol template-DNA [SEQ ID NO.: 3]:

5'-dgAgCCTTCAACCCAgTCAgCTCCTTC-CggTgggCgCggggCCATgCAACTCg-TAggACAggTgCCg-gCAgCgCTCTgggTCATTTTCggCg-3'

The oligonucleotides and the DNA-template were purchased from CODON genetic systems (Weiden/See, Austria).

Reaction mixes without added template-DNA served as negative controls.

The reaction mixes were then overlaid with 100 µl mineral oil (Sigma, M-3516) and heated to 84° C. on a Perkin Elmer Cetus GeneAmp PCR System 9600 thermostat. Two units of the enzym Deep Vent$_R$(exo⁻) DNA Polymerase (New England Biolabs, USA) were added to the mix when reaching the reaction temperature.

Single samples and negative controls were then incubated at 84° C. for different periods of time in order to check the kinetics of the amplification. 10 µl of each reaction mix was analyzed on a 2% agarose gel and made visible by staining with ethidium bromide and UV-fluorescence analysis. The amplification product could be identified as a single band by comparison with a DNA-size standard.

1.2. Time Course of the Amplification

The products of the single reaction mixes were quantified after electrophoresis. Quantification was done by serial dilution of the single reaction mixes and comparison of these dilutions with each other and with a DNA standard.

The results of this analysis is shown in table 1.

1.3. Molecular Cloning and Sequencing of an Amplification Product

After amplification the reaction mix was extracted with phenol/chloroform and chloroform followed by precipitation of the DNA with ethanol. The dried DNA was incubated in phosphorylation buffer (Boehringer Mannheim), containing 1 mM ATP and 10 units of T4 Polynucleotide Kinase (Boehringer Mannheim) in an end volume of 10 µl for one hour at 37° C. Subsequently, 1.5 µl sterile distilled water, 1.5 µl 1 M $MgCl_2$, 1 µl 1 mM dNTP (TTP, dGTP, dCTP, dATP each 250 µM) and 1 µl (2 units) Klenow-enzyme were added to the mixture and again incubated at 37° C. for one hour.

The reaction mix was separated on a preparative agarose gel, the DNA band was purified from the gel an used for ligation. The ligation of the product in a plasmid vector (pBluescript IISK+, Stratagene), which has been digested with SmaI and dephosphorylated was done by standard techniques. After transformation in competent Escherichia coli MC1061 bacteria some of the bacterial colonies were selected for plasmid DNA preparation for sequencing.

The sequencing of the cloned product with the primers M13 sequencing and M13 reverse sequencing (CODON genetic systems) was done according to the DyeDeoxy Termination method (Applied Biosystems) with the sequencing machine ABI373A.

The sequence [SEQ ID NOS.: 3 and 4] of the amplification product read:

5'-dgAgCCTTCAACCCAgTCAgCTCCTTC-CggTgggCgCggggCCATgCAACTgCCg-gCAgCgCTCTgggTCATTTTCggCg-3' (Plus Strand)

and

3'-dCTCggAAgTTgggTCAgTCgAggAAg-gCCACCCgCgCCCCggTACgTTgCggC-CgTCgCgAgACCCAgTAAAAgCCgC-5' (Minus Strand)

Thus it had been shown that the amplification product corresponds exactly to the sequence defined by the two oligonucloetide building blocks.

TABLE 1

Time course of increase in reaction product

| reaction time in minutes: | amount of product in pmol: |
|---|---|
| 0 | 0.00 |
| 20 | 0.24 |
| 40 | 0.48 |
| 60 | 1.44 |
| 120 | 4.33 |
| 240 | 8.65 |

EXAMPLE 2

Amplification of a Liner Double Stranded DNA

This example shows that it is possible to in vitro amplify a specific double stranded DNA molecule enzymatically without denaturation step.

By means of two oligonucleotides, which hybridize to two complementary DNA strands a double stranded product is formed completely avoiding the usual repeated changes of the reaction temperature between amplification and denaturation temperature.

2.1 Reaction Mix

50 µl reaction mixes were each transferred with a pipette into 0.5 µl reaction tubes (Eppendorf, Safe-Lock). the reaction mixes had the following composition:

10 mM $(NH_4)_2SO_4$
20 mM tris-HCl (pH 8.8 at 25° C.)
2 mM $MgSO_4$
each 200 µM TTP, dGTP, dATP and dCTP (PROMEGA, Wisc., USA) 0.1% (w/v) Triton X-100 (SERVA, Germany)

10 pmol oligonucleotide building block u676 [SEQ ID NO.: 1]:

10 pmol oligonucleotide building block 1755 [SEQ ID NO.: 1]:

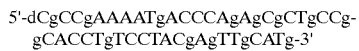

1 fmol template-DNA [SEQ ID NOS.: 3 and 5];

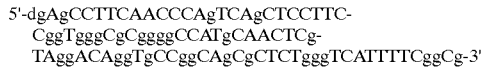

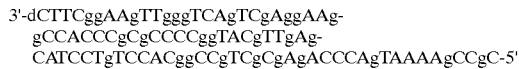

Reaction mixes without added template-DNA served as negative controls.

The reaction mixes were then overlaid each with 100 μl mineral oil (Sigma, M-3516) and heated to 84° C. on a Perkin Elmer Cetus GeneAmp PCR System 9600 thermostat. Two units of the enzym Deep Vent$_{R(exo^-)}$ DNA Polymerase (New England Biolabs, USA) were added to the mix when reaching the reaction temperature.

Samples and negative controls were then further incubated at 84° C. for 14 hours.

2.2. Visualizing

10 μl of each reaction mix was analyzed on a 2% agarose gel and made visible by staining with ethidium bromide and UV-fluorescence analysis. The amplification product could be identified as a single band by comparison with a DNA-size standard.

EXAMPLE 3

Amplification of a part of a Double Stranded DNA

This example shows, that the DNA to be amplified may be part of a larger DNA piece, especially part of a plasmid.

Plasmid pUC19 served as a template-DNA, which has been linearized with the restriction endonuclease NarI (Boehringer Mannheim). Oligonucleotide building blocks [SEQ ID NOS.: 6 and 7] used were:

and

Reaction mixes of 50 μl were pipetted into 0.5 ml reaction tubes (Eppendorf, Safe-Lock), the reaction mixes having the following contents:

10 mM $(NH_4)_2SO_4$
20 mM Tris-HCl (pH 8.8 at 25° C.)
2 mM $MgSO_4$
each 200 μM TTP, dGTP, dATP and dCTP
0.1% (w/v) Triton X-100
10 pmol oligonucleotide building block M13rev (−48)
10 pmol oligonucleotide building block M13iso
1 ng template-DNA For negative controls the same mixture as above was pipetted with the difference that template-DNA was omitted. The reaction mixtures were then overlaid with 100 μl mineral oil (Sigma M-3516). The mixtures were heated in a thermostat to 95° C. for 10 minutes (Gene Amp PCR System 9600, Perkin Elmer Cetus), cooled to 70° C. where after to each mix 2 units Deep Vent$_R$(exo$^-$) DNA Polymerase (New England Biolabs) was added.

Then samples and negative controls were further incubated at 70° C. for 14 hours. 10 μl of each mix was separated on a 2% agarose gel. The amplification product could be identified as a single band by comparison with a DNA-size standard and made visible by staining with ethidium bromide and UV-fluorescence analyses.

EXAMPLE 4

Detection of a RNA-Virus by Amplification of a Virus-specific cDNA Sequence

This example shows that cDNA can be used as a template in the process according to the present invention. A RNA-Virus (Grapevine Fanleaf Virus, GFLV) is isolated from a crude plant extract by means of specific immobilized antibodies. The viral RNA is subsequently released by heat and detergent treatment and is being reverse transcribed using a specific oligodeoxynucleotide. The cDNA is subsequently isothermally amplified.

4.1. Coating of a Surface with Specific Serum

120 μl of GFLV serum (Bioreba, Basel CH; 1:500 diluted in 0.1 M sodium carbonate buffer, pH 9.6) were pipetted into a plastic reaction tube (0.5 ml; Multi-Technology, Salt Lake City, USA) and then incubated for 1 hour at room temperature. Then, the tubes were washed three times with TPBS (137 mM NaCl, 2.7 mM KCl, 10 mM Na-phosphate; 0.1% w/v Tween 20; pH 7.4) followed by two washes with PBS (137 mM NaCl, 2.7 mM KCl, 10 mM Na-phosphate buffer, pH 7.4).

4.2. Incubation of the Samples in the Precoated Reaction Tubes

Leaf samples of grapevin (Vitis vinifera cv. French Colombard) were tested by means of GFLV-ELISA (Bioreba, CH) for infection with GFLV.

Into each precoated tube 100 μl extract of leaves of infected and non-infected grape vine, respectively was pipetted and incubated for 2 hours at 4° C. Subsequently, the antibodies were washed three times with TPBS and twice with PBS.

4.3. Oligonucleotide Building Blocks Used

The oligonucleotide building blocks amplify a part of the coat protein gene [SEQ ID NOS.: 8 and 9] of grape vine fanleaf virus.

"3'-BINE": 5' dCTAgAgTgggAAACTggTTC-3'
(EMBL Accession No: X16907, bases 3543–3562)
"GFLV5'-ENIB": 5' dgTCCAggCTTTAgCTTTTATggTA-3'
(EMBL Accession No. X16907, bases 3519–3542)

4.4. Reverse Transcription

Into each reaction tube 20 μl of a RT-buffer (50 mM Tris-HCl, pH 8.3, 7,5 mM MgCl$_2$) with additional 1 mM dCTP, 1 mM dATP, 1 mM dGTP, 1 mM TTP, 20 pmol "3'-BINE" oligonucleotide building block, 10 units RNAse inhibitor (Boehringer Mannheim, Germany), 10 units of the enzyme AMV reverse transcriptase (Boehringer Mannheim, Germany) and 0.5% Triton X-100 were pipetted. The reaction mix was incubated for 10 minutes at 65° C., followed by 10 minutes at 42° C.

4.5.1. Isothermal DNA-amplification with Deep Vent$_R$ (exo$^-$) DNA-polymerase

Into the respective reaction mixes 80 μl of a PCR buffer were pipetted [10 mM $(NH_4)_2SO_4$, 20 mM Tris-HCl, pH 8.8 at 25° C., 2 mM $MgSO_4$, 0.1% (w/v) Triton X-100] with additional of 20 pmol of the oligonucleotide "3'-BINE", 20 pmol of the oligonucleotide "GFLV 5'-ENIB" and 4 units of the enzyme Deep Vent$_R$(exo$^-$) DNA Polymerase (New England Biolabs). The reaction mixes are overlaid with 70 µl of light mineral oil (Sigma), immediately heated to 68° C. and incubated for 16 hours at this temperature.

4.5.2. Isothermal DNA-amplification with Tag DNA-polymerase

Into the respective reaction mixes 80 µl of a PCR buffer were pipetted (10 mM Tris-HCl, 50 mM KCl, 1.5 MgCl$_2$, pH 8.3 at 20° C.) with additional of 20 pmol of the oligonucleotide "3'-BINE", 20 pmol of the oligonucleotide "GFLV 5'-ENIB" and 5 units of the enzyme Taq DNA Polymerase (Boehringer Mannheim). The reaction mixes are overlaid with 70 µl of light mineral oil (Sigma), immediately heated to 68° C. and incubated for 16 hours at this temperature.

4.6. Results

10 µl of each reaction mix are separated on a 2% agarose gel by electrophoresis. The reaction products were made visible by staining with ethidium bromide and fluorescence excitation. The result was a visible band in case of the sample with infected plant material, the length of the band amounting to 44 base pairs (by comparison with the DNA-standard "50 base pair ladder", USB, Ohio). Samples with plant extract from non-infected plants did not show a band in electrophoresis.

EXAMPLE 5

Amplification of a Gen-section of Genomic DNA

This example shows that it is possible to amplify a gen-section of genomic DNA by isothermal PCR.

5.1. Preparation of Genomic DNA

DNA of the cell line A-498 (ATCC HTB 44, human kidney carcinoma) was prepared according to standard methods. This preparation was used as template-DNA.

5.2. Oligonucleotide Building Blocks [SEQ ID NOS.: 10 and 11]

appr: 5'-dgCCTAATTCTCTCATAgTCTTAATTCCCAC-3' appl-iso:
5'-dAggTAggTAAACTTgACTgCATgTTTCCAA-3'

5.3. Reaction

A 100 µl reaction mix was pipetted into a 0.5 ml reaction tube (Eppendorf, Safe-Lock, Germany), the reaction mix having the following composition:

10 mM (NH$_4$)$_2$SO$_4$ 20 mM Tris-HCl (pH 8.8 at 25° C.)

2 mM MgSO$_4$ each 200 µM TTP, dGTP, dATP and dCTP

5 µM Biotin-16-dUTP (Boehringer Mannheim)

0.1% (w/v) Triton X-100

10 pmol oligonucleotide building block appr 10 pmol oligonucleotide building block appl-iso 5 µg template-DNA As negative control the same mixture as above was pipetted, with the difference that template-DNA was omitted. The reaction mix were then overlaid with 100 µl mineral oil (Sigma M-3516). Then, the mixes were heated to 98° C. for 10 minutes, subsequently cooled down to 68° C., where after 2 units of the enzyme Deep Vent$_R$(exo$^-$) DNA polymerase (New England Biolabs) was added to each of the mixes. Thereafter, sample and neg-control was further incubated for 14 hours at 68° C.

5.4. Analysis of the Reaction

90 µl of each reaction mix were then spotted onto a nitrocellulose membrane (Hoefer Scientific Instruments, TM-NC2) by means of a Slot Blot equipment (Hoefer Sientific; PR600 Slot Blot), the membrane was heated thereafter to 80° C. for 30 minutes in a vacuumoven. Subsequently the membrane was incubated in PBS plus 5% (w/v) skimmed milk powder (Fixmilch mager from Maresi, AT) for 30 minutes at room temperature and washed three times. After an additional incubation with straptavidine-alkaline phosphatase conjugate (Amersham, UK; 1:1000 diluted) in TPBS at room temperature for 30 minutes five washing steps with PBS followed. Then, color was developed with nitro-blue-tetrazolium (0.2 mg/ml) and 5-brom-4-chlor-3-indoxyl phosphate (0.2 mg/ml), 4 mM MgCl$_2$ in 0.1 M sodiumcarbonate buffer, pH 9.6. After 30 minutes developing time one can see a clear blue color at the spot with the reaction containing human genomic DNA, the negative control showing no color.

Further analysis of the reaction mix showed some unspecific reaction products so that the amount of specific amplification could not exactly be determined.

Under the following reaction conditions the amplification from genomic DNA can be carried out much more specific (50 µl reaction mix):

20 mM Tris-HCl, pH 8.8

5 mM MgSO$_4$ each 100 µM dNTPs 0.1% (w/v) Triton X-100

10 pmol oligonucleotide building block appr 10 pmol oligonucleotide building block appl-iso 10 ng template-DNA 20 minutes of denaturation at 96° C., during this time addition of 2 units Deep Vent$_R$(exo$^-$) DNA polymerase, thereafter incubation for 1 hour at 77° C.

The product shows up as a single band after electrophoresis.

EXAMPLE 6

Detection of a Point Mutation

This example shows that it is possible to detect a point mutation by the process according to the present invention.

6.1. Oligonucleotide Building Blocks [SEQ ID NOS.: 8, 9 and 12]

| | |
|---|---|
| "3'-BINE": | 5'-dCTAgAgTgggAAACTggTTC-3' |
| "GFLV5'-ENIB": | 5'-dgTCCAggCTTTAgCTTTTATggTA-3' |
| "GFLV5'-ENIBmut": | 5'-dgTCCAggCTTTAgCTTTTATggTC-3' |

6.2. Templates

Synthetic oligonucleotides serve as templates. The two oligonucleotides [SEQ ID NOS.: 13 and 14] differ in a single base at position 24:

```
BA:  5'-GTCCAGGCTTTAGCTTTTATGGTAGAACCAGTTTCCCACTCTAG-3'
         IIIIIIIIIIIIIIIIIIIIIIII IIIIIIIIIIIIIIIIIIII
BC:  5'-GTCCAGGCTTTAGCTTTTATGGTCGAACCAGTTTCCCACTCTAG-3'
```

6.3. Reaction Mix

50 µl reaction mixes were pipetted into 0.5 ml reaction tubes (Eppendorf, Safe-Lock), the reaction mixes having the following composition:

- 10 mM (NH$_4$)$_2$SO$_4$
- 20 mM Tris-HCl (pH 8.8 at 25° C.)
- 2 mM MgSO$_4$
- each 200 µM TTP, dGTP, dATP and dCTP
- 0.1% (w/v) Triton X-100
- 10 pmol oligonucleotide building block 3'-BINE
- 10 pmol oligonucleotide building block GFLV5'-ENIB or
- 10 pmol oligonucleotide building block GFLV5'-ENIBmut
- approx. 1 fmol template-DNA (BA or BC).

For negative control the same reaction mix as above was pipetted with the difference that template-DNA was omitted. The reactions were then overlaid with 100 µl mineral oil (Sigma M-3516). The mixes were heated in a thermostat (Gene Amp PCR System 9600, Perkin Elmer Cetus) to 95° C. for 10 minutes, then cooled down to 70° C. and 2 units Deep Vent$_R$(exo⁻) DNA Polymerase (New England Biolabs) was added.

Thereafter, samples and negative controls were further incubated at 68° C. for 14 hours. 10 µl of each reaction mix were separated on an 2% agarose gel and made visible by staining with ethidium bromide and UV-fluorescence analyses. The amplification product could be identified as a single band by comparison with a DNA-length-standard. The results are summarized in table 2:

TABLE 2

| oligonucleotide combination | template | |
|---|---|---|
| | BA | BC |
| 3'BINE/GFLV5'-ENIB | + | − |
| 3'BINE/GFLV5'-ENIBmut | − | + |

+ . . . specific band on electrophoresis-gel
− . . . no band on electrophoresis-gel

EXAMPLE 7

Amplification of a Linear, Single Stranded DNA

This example shows the possibility of an enzymatically in vitro amplification of a specific single stranded DNA molecule, even if its length is higher than the sum of the lengths of both oligonucleotide building blocks.

Here, with two oligonucleotide building blocks which bind to two complementary strands a double stranded molecule is formed, without changing the reaction temperature.

7.1. Reaction Mix

50 µl reaction mixes were pipetted into 0.5 ml reaction tubes (Eppendorf, Safe-Lock); the reaction mixes having the following composition:

- 50 mM KCl
- 10 mM Tris-HCl (pH 8.3 at 20° C.)
- 1.5 mM MgCl$_2$
- each 200 µM TTP, dGTP, dATP and dCTP
- 10 pmol oligonucleotide building block u67 [SEQ ID NO.: 15]

(5'-dCAACCCAgTCAgCTCCTTCCggTgggCg-3')

- 10 pmol oligonucleotide building block 174 [SEQ ID NO.: 16]

(5'-dCgCTgCCggCACCTgTCCTACgAgTTgCATgA-3')

- 1 fmol template-DNA [SEQ ID NO.: 17]

```
5'-CAACCCAgTCAgCTCCTTCCggTgggCgCggggCATgACTATCgTCg
CCgCACTTATgACTgTCTTCTTTATCATgCAACTCgTAggACAggTg
CCggCAgCg-3'
```

Reaction mixtures without addition of template DNA served as negative control. Oligonucleotide building blocks and DNA-template were chemically synthesized by CODON genetic systems. The reaction mix was then overlaid with 100 µl mineral oil (Sigma M-3516) and heated to 84° C. on a Perkin Elmer Cetus Gene Amp PCR System 9600 thermostat. After reaching the reaction temperature 5 units of the enzyme Taq DNA polymerase (Perkin Elmer Cetus) were added to the mix, then single samples and negative controls were further incubated at 84° C. for various periods of time to be able to estimate the time course of the amplification. 10 µl of each reaction mix were separated on a 2% agarose gel and made visible by ethidium bromide staining and UV-fluorescence analysis. The amplification product could be identified by comparison to a DNA standard as a single band.

EXAMPLE 8

Detection of a Specific DNA Sequence by Template Dependent DNA Ligation 8.1. Oligonucleotides and Templates All oligonucleotide building blocks and template DNA was purchased from CODON gene stems. Oligonucleotides A and D [SEQ ID NOS.: 18–21] are chemically phosphorylated at the 5'-end.

Oligonucleotides:
- A: 5'-pdTTgTgCCACgCggTTgggAATgTA-3'
- B: 5'-dAgCAACgACTgTTTgCCCgCCAgTTg-3'
- C: 5'-dTACATTCCCAACCgCgTggCACAAC-3'
- D: 5'-pdAACTggCgggCAAACAgTCgTTgCT-3'

Template DNA [SEQ ID NO.: 22]:

```
5'-dTACATTCCCAACCgCgTggCACAA-
    CAACTggCgggCAAACAgTCgTTgCT-3'
```

Reaction Mix:

20 mM Tris-HCl (pH 7.5), 20 mM KCl, 10 mM MgCl$_2$, 1 mM DTT 0.1% NP-40 (detergent), 0.1 mM rATP Oligonucleotide A, B, C, D: 1 pmol each Template (100 fmol per reaction)

Negative controls without template DNA.

The reaction mixes (19 µl) were heated to 70° C., then the reaction was started by addition of 4 units (1 µl) of Pfu DNA Ligase (Stratagene, USA). The reaction was performed at 70° C. for 60 minutes. After incubation the reaction mixes were allowed to cool to room temperature for some minutes. 10 µl of each reaction mix were then analyzed by gel electrophoresis (2% Standard EEO agarose in 0.5 fold TBE buffer at 4° C. and 5 V/cm, 10 minutes prerun).

Result

The described mixes of the process according to the present invention gave the same results as a Ligase Chain Reaction after 25 cycles (92° C.–20 sec; 60° C.–20 sec; Stratagene LCR Kit).

EXAMPLE 9

Detection of HIV I RNA by Reverse Transcription and Subsequent Isothermal Amplification of the cDNA Non-infectious RNA was transcribed in vitro from a HIV I-standard vector and then used in dilution to characterize a specific RNA-detection. After reverse transcription of the RNA to cDNA the isothermal DNA-amplification yielded DNA fragments which could be detected by agarose gel electrophoresis. The detection limit is below 0.001 attomol.

9.1. Production of RNA by in Vitro Transcription

Starting material for in vitro transcription is the vector pBH10, in which an approx. 9 kbp HIV I cDNA was integrated on the SacI-site (Hahn et al., 1984, Nature 312: 166). The vector was amplified by standard techniques, purified and linearized by means of restriction digestion with BglI. The transcription by SP6 RNA polymerase starts on the thus linearized vector on the specific promotor region which lies approx. 50 bases upfront of the HIV sequence and runs until the next downstream at BglI site. The obtained transcript thus contains the complete cloned viral sequence plus 50 bases upstream from the multiple cloning site as well as 1470 bases downstream from the residual vector (pBH10 is a derivative of pSP64, Promega, USA). The length of the RNA thus transcribed is approx. 10,200 bases and the molecular weight approx. 3,060,000 Dalton.

9.2. Reaction Mixes

For in vitro transcription all solutions and plastic articles were liberated from RNase-activity by treatment with diethyl pyrocarbonate (DEPC). A concentration of 0.1% (v/v) DEPC in water or the respective aqueous solution was allowed to react overnight at room temperature and non-reacted DEPC was destroyed by autoclaving for 120 minutes at 121° C.

A 100 µl reaction mix comprises the following components:

0.5 µg linearized vector pBH10/BglI 1 mM each of ATP, CTP, GTP and UTP (Boehringer Mannheim, Germany)

40 units RNAsin RNase Inhibitor (Boehringer Mannheim, Germany)

20 units SP6RNA Polymerase (Boehringer Mannheim, Germany)

11 µl 10-fold concentrated reaction buffer (Boehringer Mannheim, Germany).

This mix was incubated for 14 hours at 37° C. Then, 50 units DNasI was added and incubated for 2 hours at 37° C. By addition of 0.5 M EDTA solution (pH 8.0) the EDTA concentration was leveled to 20 mM and the mixture was heated for 10 minutes to 65° C.

Two ethanol precipitations with 0.1 vol 3 M sodium acetat and 2.5 vol ethanol followed. After forming of the precipitate at −20° C. within 30 minutes, centrifugation was performed for 30 minutes at 10,000×g and the pellet was rinsed in 500 µl 70% (v/v) of ethanol. After a second precipitation it was redissolved in a volume of water reduced to 25 µl. The concentration of transcript was photometrically determined. The RNA-sample used for this example showed an extinction-coefficient of 0.092 against water at 260 nm wave length after dilution to the 100-fold volume. Accordingly, one can estimate a concentration of single stranded RNA in the undiluted solution of 0.4 µg/µl. The samples obtained were stored in aliquots of 5 µl at −20° C. for up to 2 months.

9.3. Detection of RNA Containing HIV I Sequences by Isothermal Amplification

The detection comprises cDNA synthesis from viral RNA and subsequent isothermal amplification of DNA. In this example the reverse transcription is started with the oligo-nucleotid building block HB101U699. The amplification proceeds between this oligonucleotide building block and a second oligonucleotide, HB101L725. Equipment needed are heating blocks with constant temperature with an accuracy of 0.5° C. or corresponding water baths, as well as a standard equipment for agarose gel electrophoresis.

9.4. Reaction Mix

The transcript containing the virus sequence was diluted with water on ice, so that a range of dilutions was between 1 femtomol to 0.001 attomol per µl. Dilutions were prepared immediately prior to its use. 1 µl of each RNA-dilution were transformed into a 0.5 ml Eppendorf reaction tube which contained 7 µl of reverse transcription mix. Together with the sample the 8 µl volume for reverse transcription had the following composition:

10 mM Tris-HCl buffer, pH 8.8

50 mM KCl 4 mM $MgCl_2$ 0.6% (w/v) Triton X-100 (Sigma Chemicals, USA) 0.5 mM each of dATP, dCTP, dGTP and dTTP (Promega, USA)

8 pmol oligonucleotide building block HB101U699

60 units RNAsin (Boehringer Mannheim, Germany)

2 units AMV Reverse Transcriptase (Boehringer Mannheim, Germany)

The reaction mixes were overlaid with 50 µl of light mineral oil (Sigma Chemicals, USA) and subjected on a thermocycler (Trioblock TB1, Biometra, Germany) to the following program:

65° C. for 10 minutes, 42° C. hold. After 20 minutes at 42° C. the Eppendorf tubes were left on the thermocycler and randomly 25 µl of an amplification mix was added. The reaction mixes were then incubated at 72° C. for 9 hours.

Amplification Mix 20 mM Tris-HCl buffer, pH 8.9

10 mM KCl 10 mM $(NH_4)_2SO_4$ 4 mM $MgSO_4$ 0.1% (w/v) Triton X-100 (Sigma Chemicals, USA)

0.2 mM each of dATP, dCTP, dGTP and dTTP (Boehringer Mannheim, Germany)

1 pmol/µl oligonucleotide building block HB101L725

0.8 pmol/µl oligonucleotide building block HB101U699

0.75 units Taq DNA polymerase per 25 µl (Boehringer Mannheim, Germany)

The oligonucleotides used were synthesized on aABI 392 DNA-synthesizer (Applied Biosystems, USA) with the following sequence [SEQ ID NO.:23]:

HB101U699 5'-dAgC CAT gCA AAT gTT AAA AgA gAC CA-3' and [SEQ ID NO.: 24]

HB101L725 5'-dCCC ATT CTg CAg CTT CTT CAT TgA-3'

The amplified DNA solution was analyzed at standard conditions by means of electrophoresis. To 20 µl of each reaction mix 4 µl loading buffer was added and separated in a 2% agarose gel in 0.5 fold TBE buffer at 5 V/cm. The DNA on the gel was vizualized by ethidiumbromide staining and UV-fluorescence analysis.

| 0.5 × TBE buffer: | loading buffer: |
|---|---|
| 45 mM Tris | 40% (w/v) sucrose |
| 45 mM boric acid | 0.05% (w/v) bromophenolblue |
| 1 mM EDTA | |

As result FIG. 1 shows appearance of a single band of 50 base pairs length in lanes 2 to 8, which correspond to RNA amounts of 1 fmol (lane 2) to 0.001 amol (lane 8) in dilution steps of 1 fmol, 100 amol, 10 amol, 1 amol, 0.1 amol, 0.01 amol and 0.001 amol RNA containing HIV-I sequence. Lanes 1 and 10 show reference band of 50 and 83 bases length from DNA-amplifications with cyclic, thermal denaturation ("PCR"). Blind controls, made from 1 µl of the water used for dilution are on lanes 9 and 11. Lane 12 shows the result of a blind amplification without the enzyme reverse transcriptase, lane 13 shows a blind control without Taq DNA polymerase added.

EXAMPLE 10
Detection of DNA by Means of Isothermal DNA Amplification at a Solid Phase The target DNA fragment is amplified isothermally between two oligonucleotides, one of which is immobilized at a plastic surface, the complementary other one is free in solution. For the detection the immobilized product was hybridized with a labelled probe. The label is detected by immunological means.

10.1. Isothermal Amplification of DNA on a Solid Phase

For the isothermal DNA amplification the oligonucleotide HB101725bio was biotinylated at the 5'-end and immobilized onto a streptavidine coated microplate (Xenoprobe, Xenopore, USA), 50 pmol oligonucleotide was diluted in 100 µl PBSE.TW buffer per well and slowly shaked for 1 hour. Non-bound oligonucleotide was removed by eight washings with 250 µl PBSE.TW.

1×PBSE.TW, pH 7.4, contains:

8 mM $Na_2HPO_4$ 2 mM $KH_2PO_4$ 137 mM NaCl 3 mM KCl 1.5 mM EDTA 0.1 (w/v) Tween 20 (Merck, Germany)

The washed plates were equilibrated for 30 minutes at 72° C. with 200 µl 1×amplification buffer per well:

1×amplification buffer:

20 mM Tris-HCl buffer, pH 8.9

10 mM KCl 10 mM $(NH_4)_2SO_4$ 2 mM $MgSO_4$ 0.1% (w/v) Triton X-100 (Sigma Chemicals, USA).

For the amplification reaction this amplification buffer was replaced by 100 µl amplification mix per well and the fragment to be detected was added in three different dilutions as 1 µl solution each. The microtiter plate was shaken, closed with a plastic seal (Nunc, Denmark) against evaporation and incubated for 15 hours at 72° C.:

Amplification mix:

1×amplification buffer containing 0.2 mM each of dATP, dCTP, dGTP and dTTP (Boehringer Mannheim, Germany)

1 pmol/µl oligonucleotide building block HB101U699

1.5 units Taq DNA polymerase per 100 µl (Boehringer Mannheim, Germany).

The oligonucleotide building blocks used have been synthesized on a ABI 392 DNA synthesizer (Applied Biosystems, USA) with the following sequence [SEQ ID NOS.: 23–25]:

HB101U699: 5'-dAgC CAT gCAAAT gTT AAA AgA gAC CA-3';

HB101L725bio: 5'-dCCC ATT CTg CAg CTT CTT CAT TgA-3', biotinylated at the 5'-end;

Detection-oligo: 5'-dgTT AAA AgA gAC CAT CAA TgA ggAAg-3';

with 6-carboxyfluorescein-label at the 5'-end.

10.2. Detection of the Immobilized Amplified DNA on Solid Phase

The microtiter plate was washed after amplification three times with PBSE.TW and preconditioned in the same buffer system for hybridization: 0.1 mg/ml freshly denatured herring sperm DNA (Boehringer Mannheim) was dissolved in PBSE.TW and 200 µl conditioning solution per well added for 30 minutes and incubated under shaking at 500 Rpm at 50° C. For hybridization 100 µl conditioning solution per well was used with 5 pmol detection-oligo per well. After 30 minutes hybridization under the above described conditions the plates were washed five times for 10 minutes with 250 µl PBSE.TW at 50° C.

For the immunological detection, the plates were blocked with 250 µl per well of 3% casitone (Difco, USA) in PBSE (blocking solution). After 30 minutes blocking at room temperature, the wells were incubated with anti-fluorescein isothiocyanate-antibody coupled to horseradish peroxydase (DAKO, Denmark), diluted 1:2,000 in blocking solution.

After five washings with PBSE.TW, to each well 110 µl of peroxidase substrate (ImmunoPure, Pierce, USA) was added and 25 minutes incubated. After stopping of enzyme reaction with 110 µl 4 N sulphuric acid the differences of extinction were measured at 450 nm.

After substraction of the extinction of antibody conjugate after hybridization without previous DNA amplification the following result came up:

| starting amount of template | | procedure | difference in extinction |
|---|---|---|---|
| 1 | 1 fmol | complete | 0.446 |
| 2 | 100 amol | complete | 0.318 |
| 3 | 10 amol | complete | 0.112 |
| 4 | 0 amol | complete | 0.081 |

-continued

| starting amount of template | | procedure | difference in extinction |
|---|---|---|---|
| 5 | 1 fmol | without Taq DNA polymerase | 0.076 |
| 6 | 1 fmol | without Taq DNA polymerase, without HB101U699 | 0.048 |
| 7 | 0 amol | without amplification reaction | 0.000 |

10.3. Interpretation of Data

In correlation with the initial amount of template increasing differences of extinction were measured (cf. lines 1, 2, 3 and 4). The process according to the present invention is able to amplify isothermally small amounts of template on a solid phase. In order to demonstrate the significance of the obtained values, additional blind controls were carried out. The incomplete blind controls under omission of Taq DNA polymerase (line 5) and without Taq DNA polymerase and without oligonucleotide HB101U699 (line 6) respectively, are based on the use of maximum amount of template (1 fmol) and are lower than the blind controls of a complete reaction without template (line 4). The obtained results (lines 1, 2, 3, 4) are thus not superposed to an interferring amount by nucleotide components from amplification and hybridization.

EXAMPLE 11

Detection of DNA by Isothermal Amplification with a Pair of Partially Overlapping Oligonucleotides This example demonstrates the usefulness of the isothermal DNA-amplification according to the present invention when the oligonucleotide building blocks are partially redundant. When using such a combination of oligonucleotides, a fragment is amplified which has a length smaller than the sum of the lengths of both oligonucleotides due to the overlapping of the regions on the target DNA which are homologuous to the oligonucleotidess.

11.1. Oligonucleotide Building Blocks

The oligonucleotides were synthesized on an ABI 392 DNA Synethesizer (Applied Biosystems, USA) with the following sequence [SEQ ID NO.: 26]:

HIVLAP1 5'-dAAT AgT AAg AAT gTA TAg CCC TAC CAg C AT-3' and [SEQ ID NO.:27]

HIVLAP2 5'-dTTT Tgg TCC TTg TCT TAT gTC CAg AAT-3'

The oligonucleotides were selected so that for amplification each of the two 3'-terminal bases (underlined) formed a redundant information. The amplification produce on the strand headed by oligonucleotide [SEQ ID NO.:41] HIVLAP1:

5'-dAAT AgT AAg AAT gTA TAg CCC TAC CAg CAT TCT ggA CAT AAg ACA Agg ACC AAA A-3'

Template for the isothermal amplification was a double stranded DNA fragment, which has been produced with these oligonucleotide from HIV-I-cDNA by means of cyclic heat denaturing amplification (PCR). Plasmid pBH10 (Hahn et al., 1984, Nature 312: 166) served as template for this reaction.

1 µl of dilutions of this template was mixed with 33 µl amplification mix (see below), overlaid with 50 µl light mineral oil (Sigma Chemicals, USA) and incubated for 15 hours at 70° C.

Amplification Mix:

20 mM Tris-HCl buffer, pH 8.9

10 mM KCl 10 mM $(NH_4)_2 SO_4$ 2 mM $MgSO_4$ 0.1% (w/v) Triton X-100 (Sigma Chemicals, USA)

0.2 mM each of DATP, dCTP, dGTP and dTTP (Boehringer Mannheim, Germany)

0.2 pmol/µl oligonucleotide building block HIVLAP1

0.2 pmol/µl oligonucleotide building block HIVLAP2

0.5 units Taq DNA polymerase per 33 µl (Boehringer Mannheim, Germany)

The amplified DNA-solution was analyzed under standard conditions by means of electrophoresis. 20 µl each of the reaction mixes were treated with 4 µl sample buffer and separated in a 2% agarose gel in 0.5 fold TBE buffer at 5 V/cm. DNA was vizualized on the gel via ethidium bromide staining and UV-fluorescence analysis.

| 0.5 × TBE buffer: | sample buffer: |
|---|---|
| 45 mM Tris | 40% (w/v) sucrose |
| 45 mM boric acid | 0.05% (w/v) bromophenolblue |
| 1 mM EDTA | |

Electrophoresis showed with an amount of template of 10 fmol a strong band of amplified DNA, with 1 fmol amount of template a well detectable band of product, whereas no band at all when using water as a blind control. The correct length of the product formed (55 bases) was estimated by the slightly slower migration speed compared to a 50 base long standard.

EXAMPLE 12

Detection of HIV-1 RNA by Reverse Transcription and Subsequent Isothermal Amplification of the cDNA with Modified Oligonucleotides Non-infectious RNA was in vitro transcribed from a HIV1 standard vector, and was used for the characterization of a specific RNA detection system. After reverse transcription of the RNA to CDNA the isothermal DNA amplification yields biotinylated DNA-fragments. The formed fragments were bound to streptavidine coated microtiter plates, hybridized with a fluorescence labelled probe and detected by a anti-fluorescein-antibody-enzyme conjugate. The detection limit for RNA is below 0.1 amol.

12.1. Production of RNA by In Vitro Transcription

This step is described in example 9, points 9.1. and 9.2. and was used in this example without modification.

12.2. Isothermal Amplification of Nucleic Acids from RNA Containing HIV1 Sequence This step is described in example 9, points 9.3. and 9.4. and was used with two modifications:

12.2.1. The second oligonucleotide building block used for the isothermal amplification is biotinylated at the 5'-end: BH101L725bio.

12.2.2. Two dilutions of transcript with viral sequence were produced and used in the experiments: 10 amol/µl and 0.1 amol/µl.

The oligonucleotide building blocks used were synthesized on a ABI 392 DNA Synthesizer (Applied Biosystems, USA) with the following sequence [SEQ ID NO.:23]:

HB101U699: 5'-dAgC CAT gCA AAT gTT AAA AgA gAC CA-3' and [SEQ ID NO. 24]

HB101L725bio: 5'-dCCC ATT CTg CAg CTT CTT CAT TgA-3', biotinylation at the 5'-end.
Detection Probe [SEQ ID NO. 25]:

5'-dgTT AAA AgA gAC CAT CAA TgA ggA Ag-3', 6-carboxy-fluorescein-label at the 5'-end (Synthesis with 6-FAM Amidite, Applied Biosystems, USA).

12.3. Detection of the Amplified DNA on the Solid Phase

For binding of the biotinylated DNA product streptavidin loaded microtiter plates (Xenoprobe, Xenopore, USA) were washed twice with PBSE.TW. The amplified DNA solution was diluted with 9 volumes PBSE.TW buffer, 1 µl of this solution in 100 µl PBSE.TW was denatured by boiling for 5 minutes. To each well of the microtiter plate the complete 100 µl of the denatured solutions were pipetted and shaken at 500 rpm for 30 minutes. The plates were washed twice with PBSE.TW and hybridized with the detection oligo.

The following steps for the subsequent detection process of the DNA-fragments via hybridization and antibody reaction is described in example 10, section 10.2 and was changed in the following three ways:

12.3.1. The concentration of the detection probe was 2.5 pmol per well.

12.3.2. The dilution of the anti-fluorescein isothiocyanate antibody coupled to horseradish peroxydase was 1:5, 000.

12.3.3. The incubation for color development in peroxydase substrate was 80 minutes.

12.4. Interpretation of Data

In correlation to the starting amount of template increasing differences of extinction were measured. The described process can be used to amplify isothermally small amounts of nucleic acid, while incorporating an oligonucleotide building block modified by biotinylation into the product. The amplified DNA is prone to any detection method, in which modified oligonucleotide building blocks are necessary.

In this example the amplified DNA is bound to the, solid phase via a biotin-moiety and quantified by hybridization.

| amount of template used | amplification procedure | difference of extinction |
|---|---|---|
| 1 10 amol | complete | 1.516 |
| 2 0.1 amol | complete | 0.376 |
| 3 0 amol | complete | 0.180 |
| 4 0 amol | no Taq DNA polymerase | 0.105 |
| 5 blind control with conjugate | | 0.087 |
| 6 blind control without conjugate | | 0.012 |

Blind controls can be explained as follows:
Line 3 represents the most completed blank, in which only the RNA template was omitted. Line 4 corresponds to line 3, further omitting Taq DNA polymerase, whereby in relation to the values of lines 1, 2 and 3 ten-fold volumina of amplification reaction was used. Lines 5 and 6 characterize the blind control from the detection of hybridization with and without antibody-peroxidase-conjugate.

EXAMPLE 13

Sequence Specific DNA Detection via Isothermal Amplification with Modified Oliponucleotides Target DNA was amplified isothermally using a biotinylated oligonucleotide, the formed fragments were captured onto oligonucleotide loaded microtiter plates by hybridization. The detection of the amplified DNA was performed with a streptavidin-enzyme conjugate, which binds to the modified oligonucleotide building block.

13.1. Isothermal Amplification of DNA with Modified Oligonucleotides

Template for the isothermal amplification were DNA fragments which had been produced by heat-denaturing amplification (PCR) from human DNA by means of oligonucleotide building blocks Appl30and Appr30. Dilutions of template with 20, 2 and 0.2 fmol/µl were produced and 1 µl of each was added into 50 µl amplification mix. The mixes were overlaid with 50 µl mineral oil (Sigma Chemicals, USA) and incubated for 90 minutes at 77° C. in a thermocycler (TB1, Biometra, Germany).

Amplification Mix
20 mM Tris-HCl buffer, pH 8.8
2 mM $MgSO_4$
0.1% (w/v) Triton X-100 (Sigma Chemicals, USA)
0.2 mM each of dATP, dCTP, dGTP and dTTP (Promega, USA)
0.2 pmol/µl oligonucleotide building block Appl30bio
0.2 pmol/µl oligonucleotide building block Appr30
2 units Deep $Vent_R(exo^-)$DNA polymerase per 50 µl (NEB, USA).

Oligonucleotides used were produced on an ABI 392 DNA Synthesizer (Applied Biosystems, USA) with the following sequence:

Appl30bio [SEQ ID NO.:28]:

5'-dAgg TAg gTA AAC TTg ACT gCA TgT TTC CAA-3';

at the 5'-end biotinylated,
Appl30 [SEQ ID NO.:28]:

5'-dAgg TAg gTA AAC TTg ACT gCA TgT TTC CAA-3',

Appr30 [SEQ ID NO.:29]

5'-dgCC TAA TTC TCT CAT AgT CTT AAT TCC CAC-3', and
AppCap [SEQ ID NO.30]:

5'-dgTC TTA ATT CCC ACT Tgg AAA CAT gCA-3', at the 5'-end chemically phosporylated.

13.2. Detection of the Amplified DNA on the Solid Phase

The amplified DNA was capture at the surface of microtiter plates via hybridization. For this, a chemical coupling of the capture oligo nucleotide (AppCap, see above) to the plates was performed.

Coupling Procedure:
Microtiter plates with secondary amino groups (CovaLink NH, Nunc, Denmark) were loaded with 5 pmol oligonuclide building blocks AppCap per well in 50 µl imidazole buffer (0.1 M N-methyl imidazole, pH 7.0). The coupling was started by addition of 50 µl of a 2% (w/v) 1-ethyl-3-(3-dimethylaminopropyl)-carbodiimide solution in imidazole buffer and shaken for 3 hours at room temperature. The purification of the plate was done by six subsequent washings with 0.4 n NaOH plus 0.25% (w/v) sodium dodecyl sulphate, six washings with PBSE.TW buffer followed by three washings with distilled water.

1×PBSE.TW, pH 7.4, contains:

8 mM $Na_2HPO_4$ 2 mM $KH_2PO_4$ 137 mM NaCl 3 mM KCl 1.5 mM EDTA 0.1% (w/v) Tween 20 (Merck, Germany)

Detection reaction: Preconditioning of the plate for hybridization was done by soluting 0.1 mg/ml freshly denatured herring sperm DNA in PBSE.TW and incubating 170 µl of this solution per well while shaking for 15 minutes at 50° C. at 500 Rpm.

For hybridization, the amplified DNA-solutions were denatured by boiling for 5 minutes. 1 µl denatured solution in 100 µl fresh conditioning solution was used per well. After 120 minutes hybridization at 50° C. and shaking with 500 Rpm the plate was washed three times with 200 µl PBSE.TW for 10 minutes at 50° C.

For detection of the thus immobilized biotinylated strand of the product of isothermal amplification was performed the plate were blocked with 150 µl per well of 1.5 casitone (Difco, USA) in PBSE.TW for 10 minutes at room temperature, then incubated with a streptavidine-alkaline phosphatase conjugate (Amersham, UK) for 30 minutes (1:2,000 in blocking solution).

The plates were washed six times with PBSE.TW and in 100 µl dyeing solution for 90 minutes. The difference of extinction at 405 nm was photometrically determined.

Dyeing Solution:

50 mM Tris.NaOH, pH10

150 mM NaCl 2 mM $MgSO_4$ 7 mM 4-nitrophenylphosphate

Result

| starting amount of template | | amplification procedure | difference of extinction |
|---|---|---|---|
| 1 | 20 fmol | complete | 0.573 |
| 2 | 2 fmol | complete | 0.232 |
| 3 | 0.2 fmol | complete | 0.055 |
| 4 | 0 fmol | without DeepVent$_R$ (exo$^-$) Pol. | 0.030 |
| 5 | 0 fmol | blind control of hybridization with conjugat | 0.019 |

13.3. Data Interpretation:

In correlation to the amount of template as offerted increasing differences of extinction were measured (lines 1,2,3). The process according to the present invention as here described is able to perform an isotherm amplification of small amounts of nucleic acid in which an oligonucleotide building block modified by biotinylation is incorporated into the product. Thus, the amplified DNA is available for any detection reaction in which use of modified oligonucleotide building blocks is mandatory. In this example a marker enzyme (alkaline phosphatase) conjugated with streptavidine binds to the biotinylation of the amplified DNA. The specifity of the detection of amplified DNA is secured via blind controls 4 and 5, in which a blind amplification without template and without Deep Vent$_R$(exo$^-$) DNA polymerase (line 4) and a blind hybridization without addition of amplification mix (line 5), respectively, amount to significantly lower differences in extinction then the lowerest measured value (line 3).

EXAMPLE 14

Amplification Rate of the Process of the Present Invention Within an Hour

This example shows the high amplification rate which is possible within short reaction times.

Two independent oligonucleotide/template combinations are used:

Combination 1:

Oligonucleotide building blocks:

"Appl30 "[SEQ ID NO.:28]: 5'-dAgg TAg gTA AAC TTg ACT gCA TgT TTCCAA-3'

"Appl30": 5'-dgCC TAA TTC TCT CAT AgT CTT AAT TCC CAC-3' and template "APP" (a synthetic double stranded DNA) piece with the following sequence [SEQ ID NO.:31]:

5'-dAgg TAg gTA AAC TTg ACT gCA TgT TTC CAA gTg ggA ATT AAg ACT ATg AgA gAA TTA ggC-3' were used.

Combination 2:

Oligonucleotide building blocks [SEQ ID NO.: 34]:

"synth1": 5'-dTAg gTT ACT TAg CAT TCT CCA CTT AgA CgA-3

"synth2": 5'-dCTA gAg ATA TTg TTC CAT ACA gAT CCC AgT-3 and template "Synth" (a synthetic double stranded DNA) piece with the following sequence:

5'-dTAg gTT ACT TAg CAT TCT CCA CTT AgA CgA ACT ggg ATC TgT ATg gAA CAA TAT CTC TAg-3 were used.

Reaction Mixes (50 µl):

20 mM Tris-HCl, pH 8.8

5 mM $MgSO_4$ dNTPs, 100 µM each 0.1% (w/v) Triton X-100 oligonucleotide building blocks 0.2 µM each.

Templates matching the respective building blocks: in different mixes different amounts of template were added: 200 amol, 20 amol and 2 amol.

A reaction mix without added template-DNA served as blind control.

14.1. Reaction

The reaction mixes were heated to 77° C., overlaid with mineral oil/light and the reaction was started with addition of 2 units DeepVent$_R$(exo$^-$)DNA-polymerase (NEB, USA) per reaction.

After one hour at 77° C. the reaction tubes were cooled down to room temperature within a few minutes and 10 µl thereof gelelectrophoretically analyzed (% standard EEO-agarose in 0.5 fold Tris-borate-EDTA (TBE) buffer at 4° C. and 5 V/cm, 10 min prerun). All sample reaction mixes with added matching template showed a significant band at 60 bp. Negative controls show no band.

EXAMPLE 15
Amplification of Linear, Double Stranded DNA of Various Lengths

This example shows the possibility to amplify template sequences of different length with a specific pair of oligonucleotides.

Reaction Mixes:

50 µl reaction mixes were pipetted in 0.5 ml reaction tubes (Eppendorf, Safe-Lock): The reaction mixes showed the following composition:

20 mM Tris-HCl (pH 8.8 at 25° C.)

2 mM MgSO$_4$ each 250 µM TTP, dGTP, DATP and dCTP 0.1% (w/v) Triton X-100

10 pmol oligonucleotide building block u676 [SEQ ID NO.: 1]:

5'-dgAgCCTTCAACCCAgTCAgCTCCTTCCggTgggCgCggggC-3'

10 pmol oligonucleotide building block 1755 [SEQ ID NO.: 2]:

5'-dCgCCgAAAATgACCCAgAgCgCTgCCg-
gCACCTgTCCTACgAgTTgCATg-3'

20 fmol template-DNA.

As template DNA in the different mixes the following double stranded synthetic DNA was used:

iso2 [SEQ ID NOS.: 36 and 37]:

5'-dgAgCCTTCAACCCAgTCAgCTCCTTC-
CggTgggCgCggggCCATgCAACTCg-
TAggACAggTgCCggCAgcgCTCTgggTCATTTTCggCg-3'

3'-dCTCggAAgTTgggTCAgTCgAggAAg-
gCCACCCgCgCCCCggTACgTTgAg-
CATCCTgTCCACggCCgTCgCgAgACCCAgTAAAAgCCgC-5' iso2+1 [SEQ ID NOS.: 3 and 38]:

5'-dgAgCCTTCAACCCAgTCAgCTCCTTC-
CggTgggCgCggggCACATgCAACTCg-
TAggACAggTgCCggCAgcGCTCTgtggTCATTTTCggCg-3'

3'-dCTCggAAgTTgggTCAgTCgAggAAg-
gCCACCCgCgCCCCgTgTACgTTgAg-
CATCCTgTCCACggCCgTCgCgAgACCCAgTAAAAgCCgC-5' iso2+5 [SEQ ID NOS.: 38 and 40]:

5'-dgAgCCTTCACCCAgTCAgCTCCTTCCg-
gTqqgCgCggggCAAAAACATgAACTCg-
TAggACAggTgCCggCAgcGCTCTggTCATTTTCggCg-3'

3'-dCTCggAAgTgggTCAgTCgAggAAggC-
CACCCgCgCCCCgTTTTTgTACg TTgAgCATCCTgTCCACg-
gCCgTCgCgAgACCCAgTAAAAgCCgC-5'

Negative controls were reaction mixes without template DNA.

The reaction mixes were then overlaid each with 100 µl mineral oil (Sigma M-3516) and heated to 84° C. on a Perkin Elmer Cetus Gene Amp PCR System 9600 thermostat.

After reaching the reaction temperature 2 units of the enzyme Deep Vent$_R$(exo$^-$) DNA polymerase (New England Biolabs) were added to the mix. Samples and blind controls were further incubated at 84° C. for 14 hours.

Vizualizing of the Results

The mixes were analyzed under standard conditions by means of electrophoresis. 20 µl of reaction mixes were each treated with 4 µl of sample buffer and separated in a 2% agarose gel in 0.5-fold TBE buffer at 5 V/cm. The DNA on the gel was vizualized by ethidium bromide staining and UV-fluorescence analysis.

0.5×TBE buffer (45 mM tris; 45 mM boric acid; 1 mM EDTA)

Sample buffer: 40% (w/v) sucrose; 0.05% (w/v) bromophenolblue

Results

The electrophoresis showed a significant band with the samples with template "iso2", a weaker band with the samples with template "iso2+1" and a very weak band with the samples with template "iso2+5" in the height corresponding to the product (the correct length of the products formed was estimated by comparison to a standard DNA; 50 base-pair ladder of United States Biochemicals, Ohio, USA). Reaction mixes without templates did not show any band.

EXAMPLE 16
Detection of HIV-1 Sequences by Isothermal Amplification with Modified Oligonucleotide Building Blocks This example shows the amplification of specific sequences by use of labelled oligonucleotide building blocks. Both specific oligonucleotide building blocks carry a different label so that the amplification product carries two different labels. One label (biotine) is used to simply immobilize the product onto a solid phase, so that it is apt for a further detection via the second label (fluorescence). By a dilution series of specific target molecules it is shown that the amount of product in a certain range is proportional to the initial amount of template.

Oligonucleotides used were prepared on an ABI 392 DNA Synthesizer (Applied Biosystems, USA) with the following sequence [SEQ ID NOS.: 23 and 24]:

HB101U699FAM:

Fluorescein-5'dAgC CAT gCA AAT gTT AAA AgA gAC CA-3' and

HB101L725bio:

Biotin-5'-dCCC ATT CTg CAg CTT CTT CAT TgA-3'

The template used was a double stranded synthetic DNA with the following sequence [SEQ ID NO.: 35]:

5'-dAgCCATgCAAATgTTAAAAgAgACCAT-
CAATgAAgAAgCTgCAgAATggg-3'

Reaction mix

50 µl reaction mixes were pipetted into 0.5 ml reaction tubes (Eppendorf, Safe-Lock), the reaction mixes having the following composition:

20 mM Tris-HCl (pH 8.8 at 25° C.)

5 mM MgSO$_4$ each 200 µM TTP, dGTP, dATP and dCTP 0.1% (w/v) Triton X-100

10 pmol oligonucleotide building block HB101U699FAM 10 pmol oligonucleotide building block HB101L725bio template-DNA.

For negative controls the same reaction mix as above was pipetted, however with omission of template DNA.

The reaction mixes were then overlaid with 100 µl mineral oil (Sigma M-3516), heated to 74° C. on a thermostat (Gene Amp PCR System 9600, Perkin Elmer Cetus). Then, 2 units of the enzyme Deep Vent$_R$(exo$^-$) DNA polymerase (New England Biolabs) were each added and incubated for 90 minutes.

10 µl of each reaction mix were separated on a 2%-agarose gel and made visible by staining with ethidium bromide and UV-fluorescence analysis. The amplification product could be identified by comparison with a DNA-length standard as a single band.

Detection by a Solid Phase Assay in Microtiter Plates

Streptavidin coated microtiter plates (Xenoprobe, Xenopore, USA) were washed with PBS. Then, 100 µl of the single samples of the amplification reaction which each have been diluted 1:10, 1:40 and 1:4,000, respectively, in TPBS were pipetted into the wells and shaken for 25 minutes at room temperature. Subsequently, the plate was washed three times with TPBS. 100 µl of diluted conjugate (anti-Fluorescein-alkaline phosphatase, Boehringer Mannheim, Germany; 1:10,000 in TBS) was added to each well. After incubation for one hour at room temperature with constant agitation, the plate was washed again three times with TPBS. After one additional wash with PBS into each well 100 µl of dyeing solution was added (LumiPhos plus, Lumigen, USA).

After 30 minutes incubation the luminescence was measured with a luminometer (Lucy 1, Anthos, Austria). The noise was measured from the negative controls.

| | Results: | | |
|---|---|---|---|
| Number of molecules | | Signal/Noise | |
| in the reaction | dilution 1:4,000 | 1:40 | 1:10 |
| 1 | 1 | 2 | 10 |
| 72 | 1 | 7 | 30 |
| $7.2 \times 10^3$ | 5 | 150 | |
| $7.2 \times 10^5$ | 40 | 1013 | |
| $7.2 \times 10^7$ | 71 | | |
| $7.2 \times 10^9$ | 111 | | |

EXAMPLE 17

Amplification of a Section from an Uncut Plasmid with Drimer, the Amplification Product Being Longer than the Sum of the Bases of the Two Oligonucleotide Building Blocks:

As template DNA served plasmid pUC19 which was not linearized. Oligonucleotide building blocks [SEQ ID NOS.:36 and 37] were used:

pUC19:20U1897 (5'-dAgTAgTTCgCCAgTTAATAg-3')

and

PUC19:18L1926 (5'-dgTAgCAATggCAACAACg-3')

50 µl reaction mixes were pipetted into 0.5 ml reaction tubes (Eppendorf, Safe-Lock), the reaction mixes having the following compositions:

20 mM Tris-HCl (pH 8.8 at 25° C.)

5 mM MgSO$_4$ each 200 µM TTP, dGTP, DATP and dCTP 0.1% (w/v) Triton X-100

10 pmol oligonucleotide building block pUC19:20U1897

10 pmol oligonucleotide building block pUC19:18L1926

1 ng template-DNA.

As negative control the same reaction mix as above was pipetted, with the difference that template DNA was omitted. The mixes were then overlaid with 100 µl mineral oil (Sigma M-3516). The mixes were heated on a thermostat (Gene Amp PCR System 9600, Perkin Elmer Cetus) to 74° C., then 2 units of the enzyme Deep Vent$_R$(exo$^-$) DNA polymerase (New England Biolabs) were each added and incubated for 1 hour.

10 µl of the reaction mixes were separated on a 2%-agarose gel and visualized after ethidium bromide staining and UV-fluorescence analysis. The amplification product could be identified as a single band by comparison with a DNA-length standard.

We claim:

1. A process for the exponential amplification of a nucleic acid in a reaction mix by means of at least one enzyme, wherein the reaction mix comprises a nucleic acid to be amplified and oligonucleotides having base sequences substantially complementary to base sequences of the nucleic acid to be amplified, which oligonucleotides may, under appropriate conditions, form starting points and/or chemical oligonucleotide building blocks for nucleic acid synthesis, said process comprising the steps of forming a reaction product comprising said oligonucleotides which is substantially complementary to the nucleic acid to be amplified, reacting the reaction product with oligonucleotides such that additional reaction product is formed and the nucleic acid to be amplified is amplified, whereby the steps are performed at a temperature which destabilizes the double strand form of the reaction product, and whereby said temperature is held essentially isothermal throughout amplification.

2. A process according to claim 1, wherein the at least one enzyme used for amplification is a polymerase.

3. A process according to claim 2, wherein the at least one polymerase used for amplification shows reverse transcriptase activity.

4. A process according to claim 2, wherein in addition to polymerase also a ligase is used as an enzyme for amplification.

5. A process according to claim 1, wherein at least one enzyme used for amplification is a ligase.

6. A process according to claim 1, further comprising the steps of reacting the reaction product with oligonucleotides or oligonucleotide building blocks and polymerase, at a temperature which destabilizes the double strand form of the reaction product, the temperature being held substantially isothermal, wherein the polymerase demonstrates strand displacement activity.

7. A process according to claim 6, characterized wherein at least one of the oligonucleotides used is immobilized on a carrier.

8. A process according to claim 1, further comprising carrying out the amplification at a temperature above the melting temperature of the oligonucleotides used.

9. A process according to claim 6, wherein the oligonucleotides are substantially complementary to adjacent base sequences on the nucleic acid to be amplified.

10. A process according to claim 6, further comprising using helper oligonucleotides for the improvement of amplification.

11. A process according to claim 10, wherein the oligonucleotides are exactly complementary to at least a part of the template sequence.

12. A method for diagnosis by detection of a target sequence outside a human or animal body, comprising amplifying a nucleic acid according to the process of claim 5, whereby the target sequence is detected.

13. A process according to claim 1, further comprising at least partially separating the nucleic acid to be amplified into single strands and/or transcribing the nucleic acid prior to amplification.

14. A process according to claim 7, wherein said carrier is a plastic surface.

15. A process according to claim 6, further comprising at least partially separating the nucleic acid to be amplified into single strands and/or transcribing the nucleic acid prior to amplification.

16. A method for diagnosis by detection of a target sequence outside of a human or animal body, comprising amplifying a nucleic acid according to the process of claim 6, whereby the target sequence is detected.

17. A process for the exponential amplification of a nucleic acid in a reaction mix by means of enzymes, wherein the reaction mix comprises a nucleic acid to be amplified and oligonucleotides having base sequences substantially complementary to base sequences of the nucleic acid to be amplified, which oligonucleotides may, under appropriate conditions, form starting points and/or chemical oligonucleotide building blocks for nucleic acid synthesis, said process comprising the steps of forming a reaction product comprising said oligonucleotides which is substantially complementary to the nucleic acid to be amplified, reacting the reaction product with oligonucleotides such that additional reaction product is formed and the nucleic acid to be amplified is amplified, whereby the steps are performed at a temperature which is above the melting temperature of the oligonucleotides used, whereby said temperature destabilizes the double strand form of the reaction product, and whereby said temperature is held essentially isothermal throughout amplification.

* * * * *

SEQUENCE LISTING

```
<160> NUMBER OF SEQ ID NOS: 41

<210> SEQ ID NO 1
<211> LENGTH: 41
<212> TYPE: DNA
<213> ORGANISM: synthetic construct

<400> SEQUENCE: 1
dgagccttca acccagtcag ctccttccgg tgggcgcggg g                41

<210> SEQ ID NO 2
<211> LENGTH: 51
<212> TYPE: DNA
<213> ORGANISM: synthetic construct

<400> SEQUENCE: 2
dcgccgaaaa tgacccagag cgctgccggc acctgtccta cgagttgcat g        51

<210> SEQ ID NO 3
<211> LENGTH: 92
```

```
<212> TYPE: DNA
<213> ORGANISM: synthetic construct

<400> SEQUENCE: 3
dgagccttca acccagtcag ctccttccgg tgggcgcggg gccatgcaac tcgtaggaca      60
ggtgccggca gcgctctggg tcattttcgg cg                                    92

<210> SEQ ID NO 4
<211> LENGTH: 92
<212> TYPE: DNA
<213> ORGANISM: synthetic construct

<400> SEQUENCE: 4
dctcggaagt tgggtcagtc gaggaaggcc acccgcgccc ggtacgttg agcatcctgt       60 ccacggccgt cgcgagaccc agtaaaagcc gc                                    92

<210> SEQ ID NO 5
<211> LENGTH: 93
<212> TYPE: DNA
<213> ORGANISM: synthetic construct

<400> SEQUENCE: 5
dcttcggaag ttgggtcagt cgaggaaggc cacccgcgcc ccggtacgtt gagcatcctg      60
tccacggccg tcgcgagacc cagtaaaagc cgc                                   93

<210> SEQ ID NO 6
<211> LENGTH: 25
<212> TYPE: DNA
<213> ORGANISM: synthetic construct

<400> SEQUENCE: 6
dagcggataa caatttcaca cagga                                            25

<210> SEQ ID NO 7
<211> LENGTH: 25
<212> TYPE: DNA
<213> ORGANISM: synthetic construct

<400> SEQUENCE: 7
dggcgtaatc atggtcatag ctgtt                                            25

<210> SEQ ID NO 8
<211> LENGTH: 21
<212> TYPE: DNA
<213> ORGANISM: synthetic construct

<400> SEQUENCE: 8
dctagagtgg gaaactggtt c                                                21

<210> SEQ ID NO 9
<211> LENGTH: 25
<212> TYPE: DNA
<213> ORGANISM: synthetic construct

<400> SEQUENCE: 9
dgtccaggct ttagctttta tggta                                            25

<210> SEQ ID NO 10
<211> LENGTH: 31
<212> TYPE: DNA
<213> ORGANISM: synthetic construct
```

```
<400> SEQUENCE: 10
dgcctaattc tctcatagtc ttaattccca c                              31

<210> SEQ ID NO 11
<211> LENGTH: 31
<212> TYPE: DNA
<213> ORGANISM: synthetic construct

<400> SEQUENCE: 11
daggtaggta aacttgactg catgtttcca a                              31

<210> SEQ ID NO 12
<211> LENGTH: 25
<212> TYPE: DNA
<213> ORGANISM: synthetic construct

<400> SEQUENCE: 12
dgtccaggct ttagctttta tggtc                                     25

<210> SEQ ID NO 13
<211> LENGTH: 87
<212> TYPE: DNA
<213> ORGANISM: synthetic construct
<220> FEATURE:
<221> NAME/KEY: misc_feature
<222> LOCATION: ()..()
<223> OTHER INFORMATION: Nucleotides 45-87 are n wherein n = i.

<400> SEQUENCE: 13
gtccaggctt tagcttttat ggtagaacca gtttcccact ctagnnnnn nnnnnnnnnn    60 nnnnnnnnnn nnnnnnnnnn nnnnnnn                                      87

<210> SEQ ID NO 14
<211> LENGTH: 44
<212> TYPE: DNA
<213> ORGANISM: synthetic construct

<400> SEQUENCE: 14
gtccaggctt tagcttttat ggtcgaacca gtttcccact ctag                   44

<210> SEQ ID NO 15
<211> LENGTH: 29
<212> TYPE: DNA
<213> ORGANISM: synthetic construct

<400> SEQUENCE: 15
dcaacccagt cagctccttc cggtgggcg                                    29

<210> SEQ ID NO 16
<211> LENGTH: 33
<212> TYPE: DNA
<213> ORGANISM: synthetic construct

<400> SEQUENCE: 16
dcgctgccgg cacctgtcct acgagttgca tga                               33

<210> SEQ ID NO 17
<211> LENGTH: 103
<212> TYPE: DNA
<213> ORGANISM: synthetic construct
```

<400> SEQUENCE: 17
caacccagtc agctccttcc ggtgggcgcg gggcatgact atcgtcgccg cacttatgac    60
tgtcttcttt atcatgcaac tcgtaggaca ggtgccggca gcg                    103

<210> SEQ ID NO 18
<211> LENGTH: 26
<212> TYPE: DNA
<213> ORGANISM: synthetic construct
<220> FEATURE:
<221> NAME/KEY: misc_feature
<222> LOCATION: (1)..(2)
<223> OTHER INFORMATION: Nucleotide 1 is n wherein n = p.

<400> SEQUENCE: 18
ndttgtgcca cgcggttggg aatgta                                        26

<210> SEQ ID NO 19
<211> LENGTH: 27
<212> TYPE: DNA
<213> ORGANISM: synthetic construct

<400> SEQUENCE: 19
dagcaacgac tgtttgcccg ccagttg                                       27

<210> SEQ ID NO 20
<211> LENGTH: 26
<212> TYPE: DNA
<213> ORGANISM: synthetic construct

<400> SEQUENCE: 20
dtacattccc aaccgcgtgg cacaac                                        26

<210> SEQ ID NO 21
<211> LENGTH: 27
<212> TYPE: DNA
<213> ORGANISM: synthetic construct
<220> FEATURE:
<221> NAME/KEY: misc_feature
<222> LOCATION: (1)..(2)
<223> OTHER INFORMATION: Nucleotide 1 is n wherein n = p.

<400> SEQUENCE: 21
ndaactggcg ggcaaacagt cgttgct                                       27

<210> SEQ ID NO 22
<211> LENGTH: 51
<212> TYPE: DNA
<213> ORGANISM: synthetic construct

<400> SEQUENCE: 22
dtacattccc aaccgcgtgg cacaacaact ggcgggcaaa cagtcgttgc t             51

<210> SEQ ID NO 23
<211> LENGTH: 27
<212> TYPE: DNA
<213> ORGANISM: synthetic construct

<400> SEQUENCE: 23
dagccatgca aatgttaaaa gagacca                                       27

<210> SEQ ID NO 24
<211> LENGTH: 25

```
<212> TYPE: DNA
<213> ORGANISM: synthetic construct

<400> SEQUENCE: 24
dcccattctg cagcttcttc attga                                  25

<210> SEQ ID NO 25
<211> LENGTH: 27
<212> TYPE: DNA
<213> ORGANISM: synthetic construct

<400> SEQUENCE: 25
dgttaaaaga gaccatcaat gaggaag                                27

<210> SEQ ID NO 26
<211> LENGTH: 31
<212> TYPE: DNA
<213> ORGANISM: synthetic construct

<400> SEQUENCE: 26
daatagtaag aatgtatagc cctaccagca t                           31

<210> SEQ ID NO 27
<211> LENGTH: 28
<212> TYPE: DNA
<213> ORGANISM: synthetic construct

<400> SEQUENCE: 27
dttttggtcc ttgtcttatg tccagaat                               28

<210> SEQ ID NO 28
<211> LENGTH: 32
<212> TYPE: DNA
<213> ORGANISM: synthetic construct

<400> SEQUENCE: 28
daggtaggta aacttgaact gcatgtttcc aa                          32

<210> SEQ ID NO 29
<211> LENGTH: 31
<212> TYPE: DNA
<213> ORGANISM: synthetic construct

<400> SEQUENCE: 29
dgcctaattc tctcatagtc ttaattccca c                           31

<210> SEQ ID NO 30
<211> LENGTH: 28
<212> TYPE: DNA
<213> ORGANISM: synthetic construct

<400> SEQUENCE: 30
dgtcttaatt cccacttgga aacatgca                               28

<210> SEQ ID NO 31
<211> LENGTH: 61
<212> TYPE: DNA
<213> ORGANISM: synthetic construct
```

<400> SEQUENCE: 31
daggtaggta aacttgactg catgtttcca agtgggaatt aagactatga gagaattagg        60
c                                                                        61

<210> SEQ ID NO 32
<211> LENGTH: 31
<212> TYPE: DNA
<213> ORGANISM: synthetic construct

<400> SEQUENCE: 32
dtaggttact tagcattctc cacttagacg a                                       31

<210> SEQ ID NO 33
<211> LENGTH: 31
<212> TYPE: DNA
<213> ORGANISM: synthetic construct

<400> SEQUENCE: 33
dctagagata ttgttccata cagatcccag t                                       31

<210> SEQ ID NO 34
<211> LENGTH: 61
<212> TYPE: DNA
<213> ORGANISM: synthetic construct

<400> SEQUENCE: 34
dtaggttact tagcattctc cacttagacg aactgggatc tgtatggaac aatatctcta        60
g                                                                        61

<210> SEQ ID NO 35
<211> LENGTH: 51
<212> TYPE: DNA
<213> ORGANISM: synthetic construct

<400> SEQUENCE: 35
dagccatgca aatgttaaaa gagaccatca atgaagaagc tgcagaatgg g                 51

<210> SEQ ID NO 36
<211> LENGTH: 21
<212> TYPE: DNA
<213> ORGANISM: synthetic construct

<400> SEQUENCE: 36
dagtagttcg ccagttaata g                                                  21

<210> SEQ ID NO 37
<211> LENGTH: 19
<212> TYPE: DNA
<213> ORGANISM: synthetic construct

<400> SEQUENCE: 37
dgtagcaatg gcaacaacg                                                     19

<210> SEQ ID NO 38
<211> LENGTH: 93
<212> TYPE: DNA
<213> ORGANISM: synthetic construct -continued

```
<400> SEQUENCE: 38
dctcggaagt tgggtcagtc gaggaaggcc acccgcgccc cgtgtacgtt gagcatcctg      60
tccacggccg tcgcgagacc cagtaaaagc cgc                                  93

<210> SEQ ID NO 39
<211> LENGTH: 95
<212> TYPE: DNA
<213> ORGANISM: synthetic construct

<400> SEQUENCE: 39
dgagccttca acccagtcag ctccttccgg tgggcgcggg gcaaaaacat gaactcgtag      60
gacaggtgcc ggcagcgctc tggtcatttt cggcg                                95

<210> SEQ ID NO 40
<211> LENGTH: 97
<212> TYPE: DNA
<213> ORGANISM: synthetic construct

<400> SEQUENCE: 40
dctcggaagt tgggtcagtc gaggaaggcc acccgcgccc cgtttttgta cgttgagcat      60
cctgtccacg gccgtcgcga gacccagtaa aagccgc                              97

<210> SEQ ID NO 41
<211> LENGTH: 56
<212> TYPE: DNA
<213> ORGANISM: synthetic construct

<400> SEQUENCE: 41
daatagtaag aatgtatagc cctaccagca ttctggacat aagacaagga ccaaaa         56
```